United States Patent
Roberts et al.

(10) Patent No.: US 6,595,368 B2
(45) Date of Patent: Jul. 22, 2003

(54) PRE-SEPARATOR FOR INLETS OF CASCADE IMPACTORS

(75) Inventors: Daryl L. Roberts, Blaine, MN (US); Virgil A. Marple, Maple Plain, MN (US)

(73) Assignee: MSP Corporation, Shoreview, MN (US)

( * ) Notice: Subject to any disclaimer, the term of this patent is extended or adjusted under 35 U.S.C. 154(b) by 44 days.

(21) Appl. No.: 09/733,111

(22) Filed: Dec. 8, 2000

(65) Prior Publication Data

US 2002/0070148 A1 Jun. 13, 2002

(51) Int. Cl.$^7$ ................................................. B07B 7/04
(52) U.S. Cl. .................. 209/139.1; 209/23; 209/143
(58) Field of Search ........................... 209/138, 139.1, 209/142, 143, 21, 22, 23, 28, 29, 235, 250, 247, 254; 73/28.04, 28.05, 31.07, 865.5, 863.22, 863.23

(56) References Cited

U.S. PATENT DOCUMENTS

| | | |
|---|---|---|
| 2,538,116 A | 1/1951 | May |
| 2,894,877 A * | 7/1959 | Sinden ................. 435/30 |
| 3,127,763 A | 4/1964 | Lippmann |
| 3,518,815 A | 7/1970 | McFarland et al. |
| 3,693,457 A | 9/1972 | Pilat |
| 3,949,594 A * | 4/1976 | Treaftis et al. ............. 73/28.04 |
| 4,038,057 A * | 7/1977 | Roth ........................... 55/465 |
| 4,133,202 A | 1/1979 | Marple |
| 4,255,172 A | 3/1981 | Smith |
| 4,274,846 A | 6/1981 | Smith |
| 4,321,822 A | 3/1982 | Marple et al. |
| 4,391,151 A | 7/1983 | Nelson et al. |
| 4,400,982 A | 8/1983 | Bell |
| 4,452,068 A | 6/1984 | Loo |
| 4,463,595 A | 8/1984 | Yeh et al. |
| 4,523,990 A | 6/1985 | Duyckinck |
| 4,570,494 A | 2/1986 | Dunn et al. |
| 4,640,140 A | 2/1987 | Burghoffer et al. |
| 4,725,294 A | 2/1988 | Berger |
| 4,764,186 A | 8/1988 | Langer |
| 4,827,779 A | 5/1989 | Marple et al. |
| 4,972,957 A | 11/1990 | Liu et al. |
| 5,201,231 A | 4/1993 | Smith |
| 5,343,767 A | 9/1994 | Marple et al. |
| 5,437,198 A | 8/1995 | John |
| 5,693,895 A | 12/1997 | Baxter |
| 6,294,375 B1 * | 9/2001 | Chevalier ................ 435/287.1 |

FOREIGN PATENT DOCUMENTS

| | | |
|---|---|---|
| DE | 3110871 | 10/1982 |
| DE | 3545120 | 7/1986 |
| DE | 2832238 | 3/1987 |
| GB | 1354261 | 4/1971 |
| GB | 2179273 | 3/1987 |
| JP | 560760 | 6/1981 |

* cited by examiner

*Primary Examiner*—Donald P. Walsh
*Assistant Examiner*—Joseph C Rodriguez
(74) *Attorney, Agent, or Firm*—Westman, Champlin & Kelly, P.A.

(57) ABSTRACT

A pre-separator for separating out large particles from a fluid flow has a housing forming an interior chamber with an inlet and an outlet, and a separator plate in the chamber between the inlet and outlet. The separator plate has a surface facing the inlet that is provided with a liquid carrying tank into which the flow is directed when it enters the interior chamber through the inlet. The separator plate has a series of nozzle openings therethrough adjacent its periphery to the outside of the tank. The nozzle openings adjacent the periphery of the separator plate overlie a surface of the housing adjacent the outlet. The pre-separator thus has two impaction stages that permit use across a wide range of flows. The separator plate and the housing have surfaces which are tapered so that liquid in the housing can be drained out when the housing is inverted.

10 Claims, 2 Drawing Sheets

FIG. 1

Aerosol USP Inlet — 12

10

Figure 2:
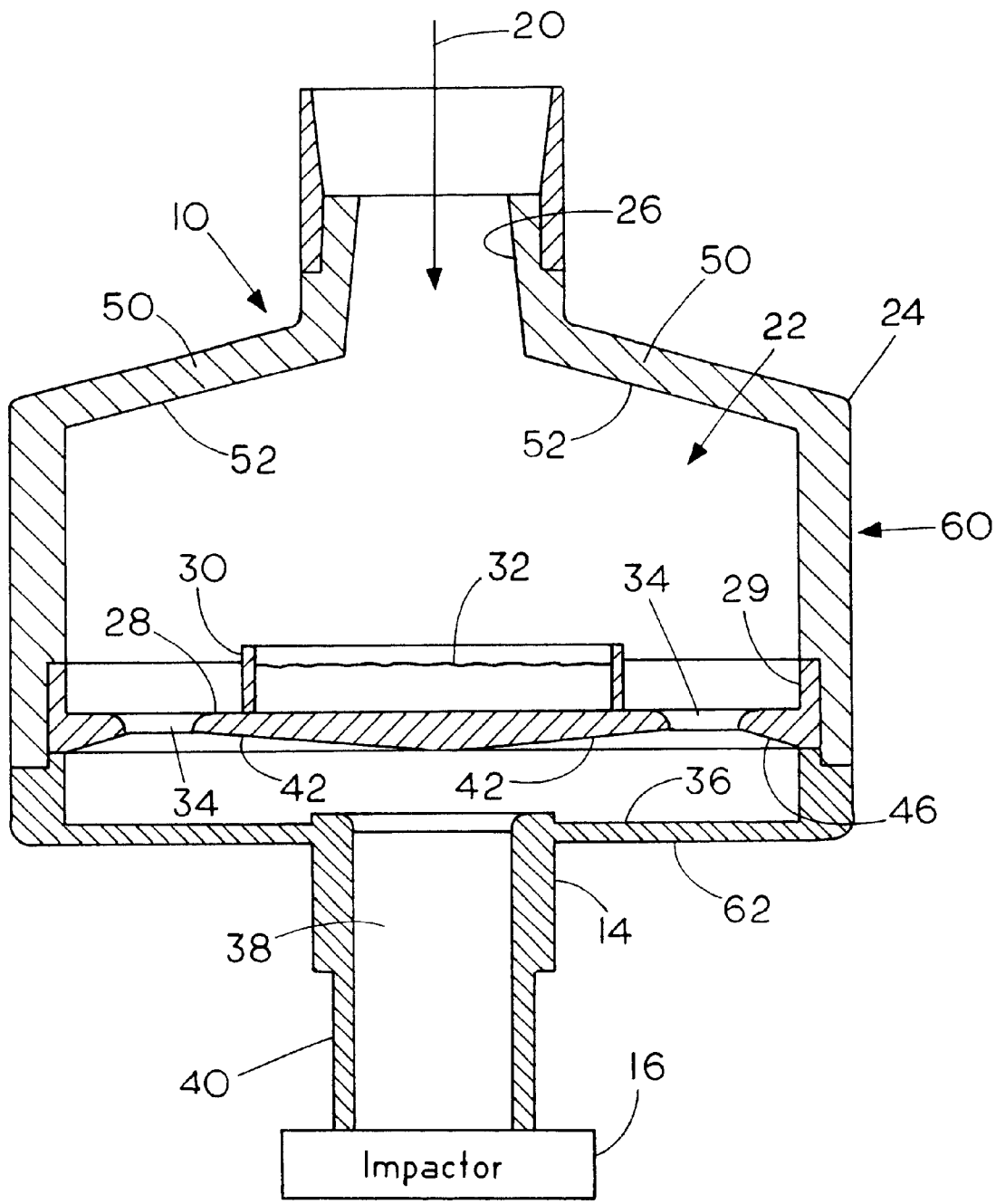

24
60

14

16 Impactor

FIG. 3

34
28
32
34
29
30
34

PRE-SEPARATOR FOR INLETS OF CASCADE IMPACTORS

CROSS REFERENCE TO RELATED APPLICATIONS

Reference is made to U.S. patent application Ser. No. 09/679,936, filed Oct. 5, 2000, for METHOD AND APPARATUS FOR CASCADE IMPACTOR TESTING OF INHALABLE DRUG THERAPIES RECOVERY FOR CHEMICAL ANALYSIS.

BACKGROUND OF THE INVENTION

In many instances, it is desired to have a pre-separator for aerosols that are being passed through a cascade impactor for classification, where the larger particles will be removed before entering the impactor.

A cascade impactor utilizing a pre-separator is shown in U.S. patent application Ser. No. 09/679,963, filed Oct. 5, 2000. The type of impactor that may utilize a pre-separator is one which has very low volume of active material that is to be analyzed, with the active material incorporated in a flow of fluid that includes inert particles that are relatively large. The larger inert particles do not enter into the analysis, but are needed for carrying the active materials in a dispersed fashion throughout the charge of gas.

A pre-separator is frequently required when measuring the aerodynamic size of particles discharged from dry powder inhalers because these formulations often contain a significant portion of diluent or carrier particles. The diluent, usually lactose, consists predominantly of particles larger than 20 micrometers, whereas the fine particles containing drug are substantially smaller than 10 micrometers. The large material causes problems for the characterization of aerodynamic size via cascade impaction because the amount is so large that it overloads the holding capacity of the first stage of the impactor. Consequently, large particles can bounce through to finer stages in the impactor, skewing the size distribution. Furthermore, when the diluent particles are very much larger than the cut point of the first stage, they may not be captured efficiently even at low loading levels.

SUMMARY OF THE INVENTION

The present invention relates to a pre-separator for use with a cascade impactor that will separate large particles that are well outside of the range of interest in the impactor from the flow. The pre-separator utilizes a two stage separator arrangement, including one stage in which a low viscosity liquid is held in a cup, and against which the direct fluid input is impacted, and a second stage separator that provides for a flow through orifices or openings arranged annularly around the center cup. The two stage impaction in the pre-separator provides the ability to operate at a much wider flow rate range than with prior single stage pre-separators. A flow in the range of 30 to 100 liters per minute can be handled. This wide range of flows permits use of a single pre-separator for several impactor designs.

The inlet fitting to this pre-separator can be a standard USP inlet. The outlet of the pre-separator can slip into an inlet fitting for the impactor unit.

BRIEF DESCRIPTION OF THE DRAWINGS

FIG. 1 is a side elevational view of a pre-separator made according to the present invention;

FIG. 2 is a vertical sectional view of the pre-separator taken on line 2—2 in FIG. 1; and FIG. 3 is a plan view of a separator plate used with the pre-separator of the present invention.

DETAILED DESCRIPTION OF THE PREFERRED EMBODIMENTS

A pre-separator indicated generally at 10 is made to provide for a separation of large particles that are fed from a source of a gas carrying particles of interest, such as a dry powder inhaler, through a standard USP inlet indicated at 12. The pre-separator outlet comprising a fitting 14 is connected to a suitable cascade impactor 16 that is used for classifying particles carried through the inlet and the pre-separator into various size classifications.

In testing dry powder inhalers, very small amounts of active ingredients are carried in each dose, for example maybe 10's of milligrams of the active components. The total weight of particles that might be added, including the inert particles such as lactose, maybe 10's of micrograms so that only 0.1 percent of the particulate material is active material. The cascade impactor that is used is to accurately classify the small amount of active particles, the total weight which may be considered to be less than 1% of the total weight of all particles in the flow of fluid to the pre-separator, and if the larger particles are permitted to enter into the cascade impactor the results are not reliable because the large particles may cause flow problems, plugging or the like.

The input flow or aerosol, which is indicated in FIG. 2 by the arrow 20, is introduced into an interior chamber 22 of the pre-separator housing 24. The input connector 26 has an opening that is directly aligned with and above a separator plate assembly 28. The central portion of the separator plate assembly 28 is solid, and has a ring 30 of material forming a small tank 32 in which a selected level of liquid, such as water, is placed. The large particles carried in the air stream indicated by the arrow 20 will enter into this tank, and strike the liquid, and the largest particles will be separated out while the air stream and smaller particles will be directed to the outer periphery of the separator plate 28. The separator plate 28 has an annular area indicated at 32 around the tank wall 30 in which a plurality of uniform size nozzles or openings 34 are provided adjacent the periphery of the separator plate, and to the outside of the wall 30. The flow of air carrying particles will go through these openings 34, and strike an imperforate collection surface 36 that is formed as part of the bottom wall of the housing 24. As shown in FIG. 3, there is only one opening 36 at each radial line or location between the wall 30 and the outer periphery of the separator plate. The surface 36 is preferably coated with a suitable adherent compound, as in conventional impactors. Particles of a second larger size impacted or separated on surface 36 will remain in place, and the rest of the flow in the smaller particles in or closer to the design range of impactor 16 will pass through a passageway 38 that is part of an output connector 40 of the pre-separator assembly. The flow through the passageway 38 will be carrying materials that have particles that are substantially reduced in size from that carried by the airflow 20, and this pre-separated flow will go into the impactor 16.

The internal surfaces of housing 24, and the separator plate 28 are designed so that they can be rinsed easily, and drained out. As can be seen, an undersurface 42 of the collection plate 28 is tapered from the central axis 44 out toward the nozzles 34. Additionally, the outer ring of the separator plate 28 has a lower surface 46 that also inclines inwardly toward the nozzles 34. That means that when the separator plate 28 is inverted, wash water and rinse water that is introduced will drain out through the openings 34 into the chamber 22. The wall 50 of chamber 22, that is opposite the surface 36, has an inner surface 52 that tapers toward the inlet connection 26 and all liquid will drain out through the inlet connection opening when the pre-separator is inverted.

The pre-separator is made in three sections that nest together. An upper section 60 that forms the chamber 22, the separator plate 28, that has an annular flange 29 that fits into a recess in section 60 and rests on a shoulder in the lower end of the upper section 60 and a lower section 62. The lower section 62 has a peripheral ring and a groove that innerfit with the lower edge of upper section 60. The upper and lower sections 60 and 62 can be welded together.

Thus, the pre-separator can be rinsed easily after use, to avoid cross contamination of particles from different dosages or tests.

The pre-separator provides for a separation, using impactor principles, of the larger particles at a wide flow range. The first or largest particles are separated by the first impaction on the separator plate, as shown, with the liquid in the tank 30, and the second size range particles are separated by impaction on surface 36. The second particles are smaller than the first particles, but larger than the designed particle range for the impactor 16. The surfaces of the pre-separator are formed to permit draining of material from the chamber so that the pre-separator can be adequately washed easily. Also, the two stage impactor in the pre-separator, which is positioned upstream from or prior to the inlet of an impactor, permits a wide useful flow range, as shown, between 30 and 100 liters per minute.

Further, the impactor 16 is designed to classify particles that are smaller than the particles classified or impacted in the pre-separator, so the two stage pre-separator provides an aerosol with larger particles removed before the aerosol is discharged into the impactor 16.

Although the present invention has been described with reference to preferred embodiments, workers skilled in the art will recognize that changes may be made in form and detail without departing from the spirit and scope of the invention.

What is claimed is:

1. A pre-separator for separating large particles from a flow of fluid comprising a housing, said housing having a peripheral wall, an inlet end wall and an outlet end wall defining an interior chamber, an inlet opening in the inlet end wall surrounded by an inner surface of the inlet end wall, the inlet opening having a central axis;

a separator plate in the chamber having a periphery supported on the peripheral wall and positioned between the inlet end wall and outlet end wall and dividing the chamber into two chamber sections, the separator plate being generally parallel to the outlet end wall and having a central imperforate portion forming an impactor surface generally perpendicular to the central axis, the housing having an outlet opening in the outlet end wall centered on the central axis;

a plurality of uniform size plate openings through the separator plate each individually located at one separate radial line location, with only one opening along each radial line and spaced from and positioned around the central portion, and each opening positioned only adjacent the periphery of said separator plate, said plate openings overlying a bottom surface of the chamber formed by the outlet end wall, the outlet end wall centered outlet opening being below the imperforate center portion of the separator plate, wherein fluid passing through the inlet opening impacts on the central imperforate portion of the separator plate and flows laterally to pass through the plate openings to strike the bottom surface, so that particles carried in the fluid will be classified according to size.

2. The pre-separator of claim 1, wherein the separator plate has a planar surface facing the inlet end wall and wherein the centeral portion of said separator plate has an annular upright wall thereon forming an open top tank facing toward the inlet opening, said tank receiving fluid entering the chamber from the inlet opening, the fluid subsequently passing through the separator plate openings at the periphery of the separator plate.

3. The pre-separator of claim 1, wherein said separator plate has a lower surface facing opposite from the inlet opening that is tapered toward the plate openings in the separator plate from a maximum thickness at the central axis of the separator plate to a lesser thickness at the plate openings, and the separator plate lower surface tapers from a maximum thickness at the periphery thereof toward the lesser thickness at the plate openings in the separator plate.

4. The pre-separator of claim 3, wherein said inner surface surrounding the inlet opening tapers to join the inlet opening such that when the inlet opening is placed in a downward position, the inner surface tapers downwardly from the peripheral wall toward the inlet opening and the lower surface of the separator plate tapers downwardly toward the separator plate openings.

5. The pre-separator of claim 1, wherein the housing is made in two sections that receive the separator plate between them, the housing sections and the separator plate being secured together to make a three part assembly.

6. The pre-separator of claim 1, wherein the fluid flow contains particles smaller than those classified in the pre-separator and wherein the outlet comprises a fitting that carries flow and is adapted to be fluidly coupled to an impactor designed for classifying particles smaller in size than the particles classified by size in the pre-separator.

7. A pre-separator for separating large particles from a flow of fluid carrying particles comprising a housing, said housing defining an interior chamber;

an inlet into the chamber having a central axis and carrying the flow of fluid;

a separator plate in the chamber having a surface generally perpendicular to the central axis receiving the flow of fluid, said separator plate having a tank formed on a surface of the separator plate and having an open top facing toward the inlet, said tank having a low viscosity liquid forming a first stage impactor for impacting first size large particles;

the housing having a bottom wall and a central outlet that is on an opposite side of the separator plate from the inlet;

a series of openings through the separator plate adjacent a periphery of said separator plate only, the plate being imperforate between each opening and the tank, said openings overlying a portion of an imperforate bottom surface peripheral portion spaced radially outward from the outlet of the chamber;

wherein fluid passing through the openings will strike the bottom surface and forms a second stage impactor for classifying second size particles which are smaller than the first size.

8. The pre-separator of claim 7, wherein said outlet is adapted to be connected to an impactor for classifying particles smaller than the second size particles.

9. The pre-separator of claim 8, wherein the flow of fluid contains large and small inert particles, the first and second size particles having a total weight substantially greater than particles passing through the outlet.

10. A pre-separator particle impactor for separating large particles from a flow of fluid carrying particles comprising a housing, said housing defining an interior chamber;

an inlet into the chamber having a central axis and carrying the flow of fluid, the housing having an inlet end wall expanding outwardly at a taper from the inlet to a side wall surrounding the chamber;

a single separator plate in the chamber dividing the chamber and having a central portion forming a solid impaction surface generally perpendicular to the central axis and aligned with the inlet such that the flow of fluid impinges thereon for forming a first stage impactor surface, the housing having an outlet end wall with a central, single outlet opening that is on an opposite side of the separator plate from the inlet;

a plurality of annularly spaced openings adjacent the periphery of said separator plate, and arranged around the central portion to carry flow outwardly from the central portion of the separator plate, said openings overlying a portion of a surface of the outlet end wall of the chamber;

the central single outlet opening being centered on the central axis and underlying the central portion of the separator plate, and being framed by a pipe forming a connector for an inlet to an impactor for classifying particles in fluid flow passing through the outlet opening.

* * * * *

UNITED STATES PATENT AND TRADEMARK OFFICE
Certificate

Patent No. 6,595,368 B2                                                                                                     Patented: July 22, 2003

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Daryl L. Roberts, Blaine, MN (US); Virgil A. Marple, Maple Plain, MN (US); and Nicholas C. Miller, White Bear Lake, MN (US).

Signed and Sealed this Third Day of November 2009.

<div style="text-align: right;">
Patrick Mackey<br>
*Supervisory Patent Examiner*<br>
Art Unit 3653
</div>